United States Patent [19]
Lindfors et al.

[11] Patent Number: 5,124,293
[45] Date of Patent: Jun. 23, 1992

[54] CATALYST FOR AROMATIZATION OF LIGHT HYDROCARBONS

[75] Inventors: Lars-Peter Lindfors, Helsinki, Finland; Erja Rautiainen, Amersfoort, Netherlands; Eeva-Liisa Lakomaa, Espoo, Finland

[73] Assignee: Neste Oy, Espoo, Finland

[21] Appl. No.: 641,908

[22] Filed: Jan. 16, 1991

[30] Foreign Application Priority Data

Jan. 16, 1990 [FI] Finland ............................ 900253

[51] Int. Cl.$^5$ .................... B01J 23/06; B01J 29/06; B01J 37/08
[52] U.S. Cl. .................................. 502/60; 502/69; 502/77; 502/78; 502/79
[58] Field of Search .............. 502/60, 77, 78, 79, 502/69

[56] References Cited

U.S. PATENT DOCUMENTS

| | | | |
|---|---|---|---|
| 3,013,984 | 12/1961 | Breck | 502/79 |
| 3,013,986 | 12/1961 | Castor | 502/79 |
| 3,013,989 | 12/1961 | Freeman, Jr. | 502/79 |

OTHER PUBLICATIONS

B. Delmon and G. F. Froment (Editors), Catalyst Deactivation 1987, pp. 639-650.

Journal of Catalysis 114, 284-290 (1988).

*Primary Examiner*—Carl F. Dees
*Attorney, Agent, or Firm*—Birch, Stewart, Kolasch & Birch

[57] ABSTRACT

The present invention concerns a catalyst suited to the aromatization reaction of light hydrocarbons. Such a heterogeneous catalyst contains zinc bound to a zeolite support material. The catalyst in accordance with the invention is prepared by adsorbing the zinc onto the surface of the zeolite support material directly from the vapour phase by way of chemisorption. The zeolite compound acting thus as the support material is here heated to a temperature which is above the condensation temperature of the zinc vapour. Advantageously, the preparation has been carried out at temperatures above 390° C. The zinc vapour has been brought to contact the zeolite support material, whereby the vapour pressure of zinc is maintained sufficiently high and the duration of its interaction with the support material sufficiently long so as to provide at least one equal amount of or, preferably, an excess of zinc in relation to the available binding sites of the support material. In order to avoid the desorption of absorbed zinc, temperature in the preparation reaction of the catalyst in accordance with the invention has been maintained below 550° C.

21 Claims, No Drawings

CATALYST FOR AROMATIZATION OF LIGHT HYDROCARBONS

The present invention relates to a catalyst for the aromatization of hydrocarbons Such a heterogeneous catalyst contains zinc bound onto a zeolite support.

Several processes associated with oil refining such as reforming and hydrocracking require a bifunctional catalyst. This is because the hydrogenation and dehydrogenation reactions take place at sites (generally at the metal species sites) different from those of the isomerization, oligomerization and cyclization reactions (occurring at various acid sites).

A common dual function catalyst is the above-mentioned zinc/zeolite catalyst whose dual function in the aromatization of n-butane includes, i.a., the following reactions:
1. Dehydrogenation of n-butane to n-butene at the zinc species.
2 Isomerization of n-butene to isobutene at the acid sites of the zeolite.
3. Oligomerization and cyclization of isobutene to olefinic naphthenes at the acid sites of the zeolite.
4 Dehydrogenation of olefinic naphthenes into aromatic compounds at the zinc species.

The conventional types of heterogeneous catalysts used for hydrocarbon reactions typically have the catalytically active species deposited on the surface of a support material The commonest methods of binding the active component onto the support material surface are impregnation, precipitation and ion exchange. The starting materials used here are compounds of the active component, for instance, its salts that are soluble in a suitable solvent. The common solvents are water, alcohols and hydrocarbons. The preparation methods of catalysts mostly require several steps. Such necessary steps are, i.a., the preparation of a solution from the catalyst component or its precursor, treatment of the support with the solution, removal of the nonreacting portion of the solution, washing, drying and calcination. Frequently, several further processing steps are required to activate the catalyst.

Thus, conventional technology is hampered by an evident drawback of the large number of the catalyst preparation steps, which easily leads to an unusable end result. The preparation of catalysts is universally recognized as an extremely delicate process requiring a very accurate control of the process steps.

Another drawback of prior art methods is associated with the need of solvents. The solvents by themselves often react with the support and change its surface structure. This is particularly the case with the use of zeolites as the support material. The acidity of the surface has a decisive effect on the activity of the catalyst. The acidity is influenced by both the type of the acid sites such as the Br.nstedt and Lewis sites as well as the number of the acid sites. The acid sites can be infuenced by, i.a., different heat treatments. When zeolites are treated with solvents, particularly water, after a heat treatment, a definite change in the distribution of the acid sites is discernible. At least a part of the acid sites then assumes an irreversibly different form. Therefore, it is obvious that the degree of acidity is uncontrollable during impregnation or ion exchange.

Further, the solvents used are often contaminated with impurities that can adversely affect the activity of the catalyst.

It is an object of the present invention to provide a novel zinc/zeolite catalyst for the aromatization of hydrocarbons. The invention is based on the concept of adding the zinc species onto the surface of the zeolite support material directly from vapour phase by way of chemisorption. The zeolite compound acting as the support material is heated to a temperature which is higher than the condensation temperature of the vapour of the zinc starting material applied. Preferably, the operating temperature should be above 390 ° C. As the zinc starting material, elemental zinc is preferably used. It is, however, also possible to employ zinc compounds that will vapourize at the temperatures indicated. As an example of a suitable zinc compound, zinc chloride may be mentioned. The zinc chloride bonded to the support forms the precursor of the catalytically active zinc species, which is obtainable by steam treatment of the support.

The vapour of the starting material is brought to contact the zeolite support material while simultaneously maintaining the vapour pressure of the vapourized starting material sufficiently high and the duration of the interaction with the support sufficiently long so as to provide at least an equal amount of or, preferably, an excess of zinc or of the zinc precursor in relation to the binding sites available on the support material. The proportion of excess zinc in relation to the zinc concentration necessary to achieve a full atomic or molecular saturation of all available binding sites on the support material surface (customarily called a monolayer coverage) is typically 1.5-1000-fold, preferably about 2-100-fold. The amount of the zinc compound necessary for a monolayer coverage can be calculated from the area determined with the help of, e.g., the BET method, and from the known molecular structure of the support material surface.

After a desired reaction time the excess vapour of starting material not bound to the zeolite support is removed from the reaction chamber. Additionally, the obtained catalyst can be posttreated to alter its activity if such a modification is desirable or necessary. As mentioned above, this will be the case for instance when zinc chloride is used as a starting compound for converting the precursor into the catalytically active zinc species.

It must be pointed out that the reaction temperature may not be so high as essentially to initiate the desorption of zinc or of the zinc precursor from the desired binding sites; in other words, excessive temperature promotes the detachment of zinc already bound on the support surface. Thus, the upper limit of applicable temperature is determined by the above-mentioned desorption temperature. The temperature is preferably kept below 550 ° C.

More specifically, the catalyst in accordance with the invention is characterized in that the catalyst is prepared by vapourizing the zinc starting material, conducting said vapour into a reaction chamber where the vapour is reacted with a zeolite support material at about 390 ... 550° C. temperature, maintaining the vapour pressure of zinc starting material sufficiently high and the duration of interaction with the support material sufficiently long so as to provide at least an equal amount of or, preferably, an excess of zinc or its precursor in relation to the binding sites available on the support material, removing the vapour of the zinc starting material not bound with the support material from the reaction space, and if necessary, posttreating the zinc/zeolite catalyst in order to modify its catalytic activity.

In the prior art, the method of binding an active metal from the vapour phase has not been applied to the preparation of catalysts used for aromatization of hydrocarbons, but instead, the ZnO/zeolite catalyst has been made by either mechanically mixing the ZnO into the support [Kanai, J. and Kawata, N., J Catal 114 (1988), p. 284] or by using aqueous solutions of salts of said metals in ion exchange with the support [Inui, T. et al., Catalyst Deactivation 1987, eds. B. Delmon and G.F. Frome, Elsevier Sci Publ., Amsterdam, p. 639].

The applied reaction conditions such as the support temperature and reaction temperature as well as the partial pressure/concentration of the vapour of the zinc starting material are process parameters subject to experimental determination. An essential characteristic of the method is that catalysts can be prepared in accordance with the method using extremely simple procedures in comparison with prior art techniques, and moreover, the active metal can be bounded only onto such sites that are controllable by the support temperature and the characteristics of the adsorbed compound.

A catalyst in accordance with the invention is prepared particularly advantageously by vapourizing elemental zinc and by reacting the zinc vapour with a zeolite support at about 430 ... 500 ° C.

In order to prepare a catalyst according to the invention, a zeolite support material can be initially heated for some time, advantageously for 1 ... 40 h, in particular for 2 ... 24 h, at 400°... 600 ° C., preferably at 430°. .. 465 ° C., before the vapour of the zinc starting material is allowed to react with the support material.

The support materials in a catalyst according to the invention can be of any zeolite materials applied in the conventional technology including such types as ZSM-5, ZSM-8, ZSM-11, ZSM-12 and ZSM-35; type A, X and Y zeolites as well as mordenite.

The reaction for binding the active metal onto the support material can be carried out at ambient pressure, yet more advantageously at reduced pressure of, e.g., 0.1 ... 100 mbar. When necessary, an inert carrier gas can be utilized to bring the vapour of the catalytically active meta or its precursor into the reaction chamber.

The catalyst in accordance with the invention is particularly well suited for the aromatization reactions of paraffines.

The invention provides significant benefits. For instance, the activity of the novel catalysts in the conversion of n-butane is equal or higher in comparison to reference catalysts. The conversion to aromatic compounds is also equal or higher on the novel catalyst. In tests performed both the conversion efficiency and selectivity to aromate compounds were found to be at a practicable level (both over 40%). Using different kinds of analysis methods (i.a. XRF, XRD and ESCA), the amount of metallic zinc was also verified to be at a practicable level, and the dispersion of zinc in the support material matrix was found to be equally good as in a catalyst prepared by the conventional impregnation method. The present method of preparing catalysts is less complicated in comparison to conventional catalysts in that there are less reaction steps than in conventional methods and the different preparation steps can be carried out without solvents sequentially in the same reaction space. The concentration of the active component in the catalyst is controlled by the surface structure of the support material, not by the applied concentration.

In the following, the invention will be illustrated with the aid of an exemplifying procedure of preparation.

EXAMPLE

Consisting of the mix of HZSM-5 zeolite and silica, the support material of the catalyst was first prepared. The zeolite was prepared as follows: 2300 g of tetrapropylammonium bromide, 100 g of sodium aluminate, 2760 g of silica gel (Ludox), 114 g of sodium hydroxide and 18500 g of water were mixed in an autoclave, the temperature was elevated to 165 ° C., and the chemicals were allowed to react for 144 h. Then, the mixture was rapidly cooled to ambient temperature, after which the product was recovered and washed with 150 l water. The obtained product was dried for 24 h at 120 ° C. and calcined for 15 h at 540 ° C. The sodium-containing zeolite was ion exchanged with a 5% w/w ammonium nitrate solution.

The ion exchanged product was dried for 24 h at 120 ° C. Next, the zeolite was calcined for 15 h at 540 ° C.

When the HZSM-5 zeolite (Si/Al=40) was ready, 100 g of zeolite, 100 ml of silica gel (Ludox AS-40) and 10 ml of water were mixed by grinding in a mortar, moulded into cakes, dried for 12 h at 115 ° C., powdered to 0.149 ... 0.35 mm particle size and calcined for 2 h at 540 ° C.

Several samples of catalysts were prepared by adsorbing zinc onto the surface of the zeolite prepared in the above-described manner. The support material lot weighing 2 ... 10 g was placed in the sample vessel of a reaction chamber where it was heat treated at 430°... 465 ° C. in a nitrogen stream of 2 ... 5 mbar pressure. The pretreatment time was 2 ... 24 h.

Metallic zinc placed in a heated source was heated to 430 ° C. and the zinc vapour was routed to reaction space. During each test the temperature of the reaction space was maintained above 430 ° C. in order to prevent the condensation of zinc onto the zeolite surface. The zinc vapour was allowed to react with the zeolite for 1 ... 4 h.

The Zn concentrations in the ready catalysts were 0.03 ... 10% w/w.

The reference catalysts were prepared with the conventional impregnation method as follows: A desired amount of zinc as zinc nitrate was dissolved in water. The dry impregnation was performed so that the solution was entirely absorbed into the pores of the support material. The amount of zinc nitrate used was 0.5 ml per 1 g of zeolite/silica support. The support material was shaken during the impregnation. Next, the catalyst was dried for 4 h at 115 ° C., and finally, calcined by heating for 2 h at 540 ° C. in an oxidizing atmosphere.

The above-described catalysts were tested in a microreactor for the conversion of n-butane into aromatics at ambient pressure in the 450°... 500 ° C. temperature range. The reaction was monitored with the help of gas chromatography. The quantity of catalyst loaded in the reactor was 5.0 g and the feed rate of n-butane into the reactor was 5 g/h. All catalysts were subjected to three product analysis runs. The reactor was heated by a through-stream of nitrogen. When the reactor temperature had reached 150° C., the nitrogen stream was cut off and the n-butane was allowed to stream through the reactor. The first sample feed to the gas chromatograph was performed after a run of 5 h at a constant temperature of 450° C. The next product analysis was performed after a run of 25 h at a reaction temperature of 500° C. The last analysis was performed after a run of 30 h at 450° C. reactor temperature. Finally, the gas stream was cut off and the reactor was purged with nitrogen till the reactor was cooled to ambient temperature. The test conditions and results are given in Table 1 below.

TABLE 1

| Catalyst load | Aromate sel. [%] [% w/w] | Zn conc. 5 h | 25 h | 30 h | Total conv. [%] 5 h | 25 h | 30 h |
|---|---|---|---|---|---|---|---|
| 586 | 0.03 | 64.8 | 69.6 | 43.8 | 10.1 | 19.2 | 10.7 |
| 627 | 0.66 | 41.4 | 37.8 | 11.2 | 36.0 | 44.6 | 35.6 |
| 628 | 0.65 | 48.4 | 40.0 | 12.6 | 40.3 | 44.2 | 35.4 |
| 629 | 1.07 | 41.8 | 32.2 | 8.9 | 37.2 | 42.2 | 34.7 |
| Ref. 1 | 1.40 | 30.6 | 38.0 | 9.9 | 37.9 | 39.7 | 33.0 |
| Ref. 2 | 0.15 | 44.4 | 61.6 | 34.6 | 17.3 | 34.3 | 19.9 |

As is evident from the results, the catalysts in accordance with the invention achieve an equal or higher degree of conversion that obtained with reference catalysts, while the selectivity to aromatic compounds is at least at an equal level.

What is claimed is:

1. A method for preparing a heterogeneous catalyst particularly suited for aromatization of light hydrocarbons, wherein said catalyst contains zinc bound onto a zeolite support material, which comprises the steps of:
   vapourizing zinc starting material to form a zinc vapour;
   reacting said zinc vapour in a reaction chamber with a zeolite support material at a temperature of about 390°. . . 550° C.;
   maintaining the vapour pressure of said zinc vapour sufficiently high and the duration of interaction between said zinc vapour and the support material sufficiently long so as to provide at least an equal amount of or an excess of zinc or its precursor relative to the binding sites available on the support material; and
   removing the zinc vapour not bound with the support material from the reaction chamber, whereby said heterogeneous catalyst is formed in said reaction chamber 2. A method for preparing a catalyst in accordance with claim 1, wherein the zinc starting material is elemental zinc.

3. A method for preparing a catalyst in accordance with claim 2, wherein the zinc vapour is reacted with the zeolite support material at a temperature of about 430° to 500° c.

4. A method for preparing a catalyst in accordance with claim 2, wherein the zinc vapour is reacted with the zeolite support material at a pressure of 1 to 100 mbar.

5. A method for preparing a catalyst in accordance with claim 2, wherein the zeolite support material is first heated for 1 to 40 hours, at a temperature of 400° to 600° C. before the zinc vapour is reacted with the zeolite support material.

6. A method for preparing a catalyst in accordance with claim 1, wherein the zeolite support material is of the type ZSM-5, ZSM-8, ZSM-11, ZSM-12, ZSM-35, A, X. Y or mordenite.

7. A method for preparing a catalyst in accordance with claim 1, wherein the formed heterogeneous catalyst is posttreated by heating.

8. A method for preparing a catalyst in accordance with claim 1, wherein said formed heterogeneous catalyst is posttreated so as to modify its catalytic activity.

9. A method for preparing a catalyst in accordance with claim 8, wherein the zinc starting material is elemental zinc.

10. A method for preparing a catalyst in accordance with claim 8, wherein the zinc vapour is reacted with the zeolite support material at a temperature of about 430° to 500°C.

11. A method for preparing a catalyst in accordance with claim 8, wherein the zinc vapour is reacted with the zeolite support material at a pressure of 1 to 100 mbar.

12. A method for preparing a catalyst in accordance with claim 8, wherein the zeolite support material is first heated for 1 to 40 hours, at a temperature of 400° to 600° C. before the zinc vapour is reacted with the zeolite support material.

13. A method for preparing a catalyst in accordance with claim 8, wherein the zeolite support material is of the type ZSM-5, ZSM-8, ZSM-11, ZSM-12, ZSM-35, A, X. Y or mordenite.

14. A method for preparing a catalyst in accordance with claim 8, wherein the formed heterogeneous catalyst is posttreated by heating.

15. A method for preparing a catalyst in accordance with claim 1, wherein the zeolite support material is first heated for 2 to 24 hours at a temperature of 430° to 465° C. before the zinc vapour is reacted with the zeolite support.

16. A method for preparing a catalyst in accordance with claim 1, wherein the zinc starting material is elemental zinc; the zinc vapour is reacted with the zeolite support material at a temperature of about 430°-500° C. at a pressure of 1 to 100 mbar; and the formed heterogeneous catalyst is posttreated by heating.

17. A method for preparing a catalyst in accordance with claim 16, wherein the zeolite support material is first heated for 1 to 40 hours at a temperature of 400° to 600° C. before the zinc is vapour is reacted with the zeolite support material.

18. A method for preparing a heterogeneous catalyst suited for aromatization of light hydrocarbons, wherein said catalyst contains zinc bound onto a zeolite support material, which comprises the steps of:
   vapourizing elemental zinc starting martial to form zinc vapour;
   reacting said zinc vapour in a reaction chamber with a zeolite support material at a temperature of about 390° to 550° C. at a pressure of 1 to 100 mbar;
   maintaining the vapour pressure of said zinc vapour sufficiently high and the duration of interaction between said zinc vapour and the support material sufficiently long so as to provide at least an equal amount of or an excess of zinc or its precursor relative to the binding sites available on the support material;
   removing the zinc vapour not bound to the support material from the reaction chamber, whereby said heterogeneous catalyst is formed in said reaction chamber; and
   posttreating said formed catalyst by heating.

19. The method of claim 18, wherein the zinc vapour is reacted with the zeolite support material at a temperature of about 430° to 500° C.; and wherein the zeolite support material is first heated for 1 to 40 hours at a temperature of 400° to 600° C. before the zinc vapour is reacted with the zeolite support material.

20. A heterogeneous catalyst particularly suited for aromatization of light hydrocarbons, said catalyst containing zinc bound onto a zeolite support material, wherein said catalyst is formed by a process which comprises the steps of:

vapourizing zinc starting material to form a zinc vapour;

reacting said zinc vapour in a reaction chamber with a zeolite support material at a temperature of about 390° to 550° C.;

maintaining the vapour pressure of said zinc vapour sufficiently high and the duration of interaction between said zinc vapour and the support material sufficiently long so as to provide at least an equal amount of or an excess of zinc or its precursor relative to the binding sites available on the support material; and removing the zinc vapour not bound with the support material from the reaction chamber, whereby said heterogeneous catalyst is formed in said reaction chamber.

21. A heterogeneous catalyst particularly suited for aromatization of light hydrocarbons, said catalyst containing zinc bound onto a zeolite support material, wherein said catalyst is formed by a process which comprises the steps of:

vapourizing elemental zinc starting martial to form zinc vapour;

reacting said zinc vapour in a reaction chamber with a zeolite support material at a temperature of about 390° to 550° C. at a pressure of 1 to 100 mbar;

maintaining the vapour pressure of said zinc vapour sufficiently high and the duration of interaction between said zinc vapour and the support material sufficiently long so as to provide at least an equal amount of or an excess of zinc or its precursor relative to the binding sites available on the support material;

removing the zinc vapour not bound to the support material from the reaction chamber, whereby said heterogeneous catalyst is formed in said reaction chamber; and posttreating said formed catalyst by heating.

* * * * *